United States Patent [19]

Wirz et al.

[11] Patent Number: 5,223,432
[45] Date of Patent: Jun. 29, 1993

[54] PROCESS FOR PREPARING OPTICALLY PURE (S)-α-((TERT-BUTYLSULFONYL)METHYL)-HYDROCINNAMIC ACID USING PROTEASE

[75] Inventors: Beat Wirz, Reinach, Switzerland; Wolfgang Wostl, Grenzach-Wyhlen, Fed. Rep. of Germany

[73] Assignee: Hoffmann-La Roche Inc., Nutley, N.J.

[21] Appl. No.: 756,027

[22] Filed: Sep. 6, 1991

[30] Foreign Application Priority Data

Sep. 12, 1990 [CH] Switzerland .......................... 2956/90

[51] Int. Cl.[5] .......................... C12P 7/40; C12P 11/00
[52] U.S. Cl. .......................... 435/280; 435/130
[58] Field of Search .......................... 435/280, 130, 136

[56] References Cited

U.S. PATENT DOCUMENTS

| | | | |
|---|---|---|---|
| 3,963,573 | 6/1976 | Stauffer | 195/29 |
| 4,259,441 | 3/1981 | Bauer | 435/23 |
| 4,262,092 | 4/1981 | Bauer | 435/280 |
| 4,629,701 | 12/1986 | Sakimae et al. | 435/130 |
| 4,668,628 | 5/1987 | Dahod et al. | 435/135 |
| 4,898,822 | 2/1990 | Asada et al. | 435/121 |
| 5,037,747 | 8/1991 | Coffen et al. | 435/125 |
| 5,061,629 | 10/1991 | Coffen et al. | 435/280 |

FOREIGN PATENT DOCUMENTS

| | | |
|---|---|---|
| 30797/89 | 9/1989 | Australia . |
| 325954 | 1/1989 | European Pat. Off. . |
| 325971 | 1/1989 | European Pat. Off. . |
| 0332008 | 2/1989 | European Pat. Off. . |
| 57-94295 | 12/1980 | Japan . |
| 105159 | 5/1984 | Japan . |

OTHER PUBLICATIONS

Biotech. Tech. vol. 3 No. 5, 1989 pp. 339-344.
Biocatalysis, 1987, vol. 1 pp. 87-88.
J. Org. Chem. 51, 1986, pp. 1003-1006.
Tetrahedron Letters vol. 28 No. 12 1987 pp. 1303-1306.
Translation Corresponding to JP 57-94295.
Chen et al., (1986), J. Chem. Soc., Chem: Commun. 1986, 1514.
Uchida, I et al, CA 114(25):247790g Nov. 7, 1990.

*Primary Examiner*—David M. Naff
*Assistant Examiner*—S. Saucier
*Attorney, Agent, or Firm*—George M. Gould; George W. Johnston; Ellen C. Coletti

[57] ABSTRACT

Optically pure (S)-α-[(tert-butylsulfonyl)methyl]-hydrocinnamic acid of the formula

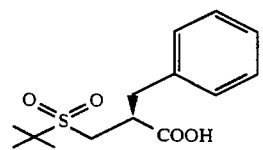

I is prepared from racemic (RS)-α-[(tert-butylsulfonyl)-methyl]hydrocinnamic acid esters of the formula

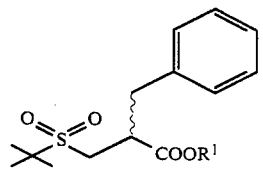

II wherein R[1] is C$_{1-4}$-alkyl, by protease-catalyzed selective hydrolysis in emulsion in an aqueous medium at a controlled pH value between about 6.5 and 8.5.

7 Claims, No Drawings

PROCESS FOR PREPARING OPTICALLY PURE (S)-α-((TERT-BUTYLSULFONYL)METHYL)HYDROCINNAMIC ACID USING PROTEASE

BRIEF SUMMARY OF THE INVENTION

The present invention relates to a novel process for the preparation of optically pure (S)-α-[(tert-butylsulfonyl)methyl]hydrocinnamic acid of the formula

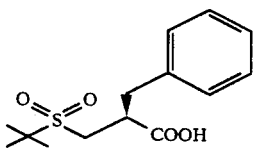

by the enzymatic-kinetic resolution of racemic (RS)-α-[(tert-butylsulfonyl)methyl]hydrocinnamic acid esters of the formula

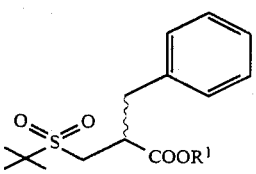

wherein $R^1$ is $C_{1-4}$-alkyl.

DETAILED DESCRIPTION OF THE INVENTION

The present invention relates to a novel process for the preparation of optically pure (S)-α-[(tert-butylsulfonyl)methyl]hydrocinnamic acid of the formula

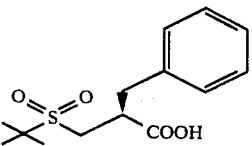

by the enzymatic-kinetic resolution of racemic (RS)-α-[(tert-butylsulfonyl)methyl]hydrocinnamic acid esters of the formula

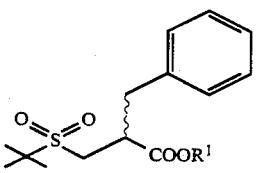

wherein $R^1$ is $C_{1-4}$-alkyl.

The term "$C_{1-4}$-alkyl" used in this description denotes straightchain and branched alkyl groups with 1–4 carbon atoms such as methyl, ethyl, propyl, isopropyl, butyl and the like, preferably methyl or ethyl, particularly ethyl.

In the formulas given in the present description, a thick, tapering line ( ▬ ) signifies a substituent having the β-orientation (that is, above the plane of the molecule or of the page), a hatched line ( ⋮ ) signifies a substituent having the α-orientation (that is, below the plane of the molecule or of the page) and a wavy line ( ∫ ) signifies a substituent having the α- or β-orientation or mixtures of these isomers.

It has been found in accordance with the invention that the S-enantiomer of formula II is hydrolyzed selectively to the S-enantiomer of formula I when the racemic mixture of formula II is subjected to an enzymatic hydrolysis using a protease enzyme.

The enzymatic hydrolysis in accordance with the invention therefore leads to the 2R-enantiomer of a compound of formula II, that is, to a compound of the formula

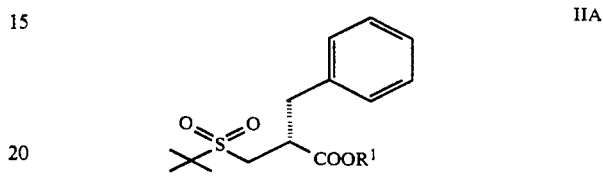

wherein $R^1$ has the significance given above, in admixture with the 2S-enantiomer of formula I. These compounds can be separated readily according to usual methods.

The selectively of certain microorganisms or certain enzymes, which have been obtained from microorganisms or vertebrate organs, permits their potential use for the preparation of enantiomer-pure intermediates from racemic mixtures. The desired enantiomeric molecule can thereafter be converted into the target compound. The resolution of isomers catalyzed by a microorganism or an enzyme provides an attractive alternative to the more traditional and expensive methods such as chemical resolution and high-pressure liquid chromatography of diastereomeric derivatives.

Kato et al. have reported that Corynebacterium equi IFO 3730 is capable of enantioselectively hydrolyzing various esters (Tetrahedron Letters, volume 28, No. 12, 1987, pages 1303–1306). In their studies the microorganism was used for the asymmetric hydrolysis of 2-benzyloxy-substituted alkane- and aryl-alkanecarboxylic acid esters. The unreacted lower alkyl esters were recovered in the optically active S-form in a high enantiomeric excess (>99% e.e.). It was also established that the replacement of the alkyl or alkenyl residue of the substrate with a phenylmethyl group gave rise to a reversal of the stereoselectivity, that is, the compound was obtained in the optically active R-form, likewise in high enantiomeric purity.

Kitazume et al. have described a process for the asymmetric hydrolysis of 2-fluoro-2-methylmalonic acid diesters with esterase from hog liver, in accordance with which the optically active (−)-2-fluoro-2-methylmalonic acid monoesters were obtained, but in low enantiomeric purity. A microbial hydrolysis of 2-fluoro-2-substituted malonic acid diesters with esterase and cellulase, whereby the optically active (+)- or (−)-2-fluoro-2-substituted malonic acid monoesters were obtained, has also been described (J. Org. Chem., 51, 1986, pages 1003–1006).

Iuchijima et al. have described a process for the production of optically active 2-chloro- and 2-bromo-substituted alkyl esters and acids by the asymmetric hydrolysis of racemic mixtures of the esters, whereby the microorganisms Rhizopus, Mucor, Aspergillus, Candida, Pseudomonas, Alkaligenes, Achromobacter and Bacillus or enzymes obtained from these microorganisms were used (published Japanese Patent Application [Kokai] No. 57-94.295 [1982]).

U.S. Pat. No. 4,668,628 (Dahod et al.) describes a process for the enzymatic resolution of racemic mixtures of partially watersoluble esters which comprises bringing the racemic mixture into contact with a Candida lipase in order to hydrolyze this enzymatically. A specific example is the Candida lipase-catalyzed hydrolysis of methyl D,L-2-chloropropionate.

European Patent Publications 0.325.954 and 0.325.971 (both Coffen et al.) describe a process for the enzymatic resolution of racemic hydroxy-substituted benzopyrancarboxylic acid esters or arylalkanoic acid esters which comprises reacting the racemic mixture with a Pseudomonas lipase in solution or in suspension in an aqueous medium at a controlled pH value between about 5 and about 10 and, respectively, 9 in order to hydrolyze this enzymatically.

Björkling et al. have described a process in accordance with which prochiral or racemic arylmethyl-substituted dialkyl malonates can be converted by α-chymotrypsin-catalyzed enantioselective hydrolysis into the corresponding optically active monoalkyl esters (Biocatalysis, 1987, volume 1, pages 87-98).

Pugnière et al. have reported that optically active aromatic amino acids can be produced by protease-catalyzed enantioselective hydrolysis of the corresponding alkyl esters in the form of emulsions of water with organic water-imiscible solvents, whereby the protease is fixed to aluminium oxide (Biotechnology Techniques, volume 3, No. 5, 1989, pages 339-344).

An important disadvantage of enzyme-catalyzed kinetic resolutions is especially the fact that the specificity of the enzyme for a given substrate cannot for the most part be predicted, since no useful models exist which, for an enzyme-catalyzed kinetic resolution of a potential substrate, permit a prediction with respect to the stereochemistry.

For performing the enzymatic resolution in accordance with the invention, the compound of formula II is firstly emulsified while warming, optionally in the presence of a co-solvent, with an aqueous phase and this is subsequently treated with the enzyme. The emulsification is effected at a temperature of 15°-55° C., preferably 35°-45° C., so that the compound of formula II is partially emulsified in the form of a melt. The emulsion contains 0.1-15% (wt./vol.), preferably 6-10%, of the compound of formula II. If a co-solvent is used, then its amount is 0.1-5% (vol./vol.), preferably 1.0-5%. As co-solvents there come into consideration the usual water-miscible polar organic solvents such as alcohols, for example, methanol or ethanol, acetone, dimethyl sulfoxide and the like. Water is used as the aqueous phase, with ordinary tap water which, if desired, can contain salts such as calcium chloride, magnesium chloride, sodium chloride and the like or buffer salts such as sodium phosphate and the like preferably being used. The amount of salt is preferably chosen so that the aqueous phase is 5-500 mM.

As protease enzymes there can be used those which are obtained from vertebrates or microorganisms, preferably microorganisms, such as α-chymotrypsin, HT Proteolytic 200 (a neutral bacterial protease obtained from Bacillus amyloliquefaciens (subs), Solvay Enzymes GmbH & Co. KG, formerly Miles Kali-Chemie GmbH & Co. KG, Hans-Böckler-Allee 20, 3000 Hannover-Kleefeld); Optimase (an alkaline protease, obtained by the controlled fermentation of Bacillus licheniformis, microbial serine proteinase, Solvay Enzymes GmbH & Co. KG, formerly Miles Kali-Chemie GmbH & Co. KG, Hans-Böckler-Allee 20, 3000 Hannover-Kleefeld); Savinase (an endoprotease of the serine type, produced by submerged fermentation of a microorganism which is an alkalophilic Bacillus species, NOVO, 2880 Bagsvaerd, Denmark); Alcalase (an endoprotease of the serine type, produced by submerged fermentation of a microorganism which is a selected strain of Bacillus licheniformis, NOVO, 2880 Bagsvaerd, Denmark); Prozyme (manufactured by a unique fermentation process of a selected strain belonging to Aspergillus which is cultured on the wheat bran and the enzyme is extracted with water and purified by fractionation with ethanol, Amano Pharmaceutical Co, Ltd, Nagoya, Japan) and the like. The use of Optimase, Savinase and Alcalase is preferred, that of Optimase being particularly preferred. The ratio of compound of formula II to enzyme is chosen so that the hydrolysis has finished after about 24 hours.

The enzymatic hydrolysis is carried out at a pH of about 6.5 to 8.5, preferably at a pH of about 7.5. Any usual methods can be used to maintain the pH value of the reaction mixture in the aforementioned range. The automatic titration with a base or the use of buffers can be mentioned among the preferred methods. The automatic titration is conveniently carried out with an aqueous base such as sodium hydroxide solution or potassium hydroxide solution. In this case, a 0.1-5M, preferably 1-2M, solution is advantageously used.

In carrying out this enzymatic hydrolysis the racemic mixture of formula II, is emulsified in an aqueous medium and reacted with preferably bacterial protease. In general, it is preferred to use the enzyme in a catalytically-active amount. Unquestionably, in order to obtain best results the necessary determination of a catalytically-active amount of a particular enzyme will depend on factors which are familiar to a person skilled in the art. These factors include the amount of starting material, the origin of the enzyme, the activity of the enzyme, the purity of the enzyme and the like. An excess of a catalytically-active amount of the protease can be used, but no improvement in the result is achieved by using a large excess of enzyme.

As mentioned above, the enzymatic hydrolysis of the racemic compound of formula II yields the compound of formula I in admixture with the compound of formula IIA. These compounds can be separated readily as soon as the enzymatic hydrolysis has stopped, namely by immediate extraction of the reaction medium with a suitable organic solvent. Any usual separation method can be used to isolate the compound of formula I from the compound of formula IIA. Extraction and chromatography can be mentioned among the usual methods for separating these two compounds.

An important aspect of the process in accordance with the invention is the achievement of a simple, efficient and economical racemate resolution by combining suitable special reaction conditions such as the emulsification of the substrate by warming, the use of simple aqueous media, the utilization of a high substrate concentration and the use of a protease, especially a cheap microbiological protease, which not only remains active, but also enantioselective under these special conditions (elevated temperature and high substrate concentration).

The compounds obtainable according to the process in accordance with the invention are useful intermediates for the preparation of renin inhibitors which can be used for the treatment of high blood pressure. Processes for the preparation of such renin inhibitors from compounds such as those which can be manufactured in accordance with the invention will be familiar to a person skilled in the art and are described in the patent literature, for example in EPA 0 332 008 (Branca et al.).

The following Examples illustrate the present invention in more detail, without limiting it.

In order to determine the enantiomeric purity, the α-[(tert-butylsulfonyl)methyl]hydrocinnamic acid obtained was reacted with (R)-(+)-α-methyl-p-nitrobenzylamine according to a method of E. Bald, K. Saigo and T. Mukaijama (Chem. Letters, 1975, 1163). The diastereomers obtained were separated by gas chromatography over a capillary column PS 086 (15 m, 50°–300° C.).

EXAMPLE 1

1.60 g (5.12 mmol) of ethyl (RS)-α-[(tert-butylsulfonyl)methyl]hydrocinnamate were treated with 50 ml of aqueous 5 mM calcium chloride solution and the reaction mixture was warmed to 38° C. while stirring. The pH value was adjusted to 7.5 with 1N sodium hydroxide solution. The hydrolysis was started by the addition of 150 mg of Savinase 6.0 T (NOVO, 2880 Bagsvaerd, Denmark). The pH value was held constant at 7.5 using automatic titration by dosing-in 1N sodium hydroxide solution while stirring vigorously at 38° C. After a consumption of 2.39 ml of 1N sodium hydroxide solution (after 21.3 hours), the reaction mixture was washed twice with 50 ml of ethyl acetate. The aqueous phase was acidified to pH 2.2 with 25% hydrochloric acid and extracted twice with 50 ml of ethyl acetate. The organic phase was dried over magnesium sulfate and evaporated at 1200 Pa/40° C., whereby there were obtained 690 mg (2.42 mmol, 47%, 94% of theory) of (S)-α-[(tert-butylsulfonyl)methylhydrocinnamic acid in the form of white crystals, which had an enantomeric excess of >99%. In order to determine the purity by gas chromatography, the compound obtained was silylated and likewise had a purity of >99%.

EXAMPLE 2

The hydrolysis of 1.60 g (5.12 mmol) of ethyl (RS)-α-[(tert-butylsulfonyl)methyl]hydrocinnamate was carried out in a manner analogous to Example 1 in the presence of 25 ml of aqueous 5 mM calcium chloride solution and 100 mg of Alcalase 2.0 T (NOVO, 2880 Bagsvaerd, Denmark). After a consumption of 2.47 ml of 1N sodium hydroxide solution (after 21.3 hours), the reaction mixture was worked-up analogously to Example 1, whereby there were obtained 700 mg (2.46 mmol, 48%, 96% of theory) of (S)-α-[(tert-butylsulfonyl)methyl]hydrocinnamic acid, which had not only an enantiomeric excess, but also a gas chromatographical (GC) purity of, in each case, >99%.

EXAMPLE 3

54 g of calcium chloride were added to 97 l of tap water to give a 5 mM solution. The solution was thermostatized to 39°–40° C. while stirring. 6.50 kg of molten ethyl (RS)-α-[(tert-butylsulfonyl)methyl]hydrocinnamate (87% GC) were poured slowly into the warm solution while stirring. The pH value of the emulsion was 7.9. The hydrolysis was started by the addition of 300 g of Optimase M 440 and the pH value was held constant at 7.5 by dosing-in 1N sodium hydroxide solution using automatic titration while stirring. After a consumption of 9.6 l of 1N sodium hydroxide solution (after 22.5 hours), 3 g of DICALITE Speedex and 10 l of ethyl acetate were added to the reaction mixture while stirring and the suspension was filtered. The filtrate was subsequently extracted with 40, 30 and 20 l of ethyl acetate (total amount 90 l). For the rapid phase separation, 2, 0.5 and, respectively, 0.2 kg of sodium sulfate (total amount 2.7 kg) were added each time. The three organic phases were dried over magnesium sulfate and evaporated at 1200 Pa/40° C., whereby 2.39 kg of ethyl (R)-α-[(tert-butylsulfonyl)methyl]hydrocinnamate were obtained. The aqueous phase was adjusted to pH 2.2 with 1.5 l of 25% hydrochloric acid and extracted with 25 and 20 l (total amount 45 l) of ethyl acetate. The first phase separation was accelerated by the addition of 0.2 kg of sodium sulfate. The two organic phases were dried over magnesium sulfate and evaporated at 1200 Pa/40° C., whereby there were obtained 2.22 kg (7.716 mol) of (S)-α-[(tert-butylsulfonyl)methyl]hydrocinnamic acid, which had an enantiomeric excess and a gas-chromatographical purity of, in each case, >99%.

EXAMPLE 4

A solution of 79 g (0.25 mol) of ethyl (RS)-α-[(tert-butylsulfonyl)methyl]hydrocinnamate in 105 ml of dimethyl sulfoxide was added dropwise while stirring vigorously to 6.2 l of water at 30° C. The pH value was adjusted to 7.5 with 0.1N sodium hydroxide solution. The hydrolysis was started by the addition of 1.05 g of α-chymotrypsin. The pH value was held constant at 7.5 using automatic titration by dosing-in 0.043N calcium hydroxide solution of 30° C. After a consumption of 2.67 l of 0.043N calcium hydroxide solution (after 19.5 hours), the reaction mixture was extracted three times with 2 l of ethyl acetate. The aqueous phase was acidified to pH 2.5 with 5% hydrochloric acid and extracted twice with 2 l of ethyl acetate. The organic phases were filtered over DICALITE Speedex, combined and dried over magnesium sulfate. After evaporating the solvent and drying the residue in a high vacuum, there were obtained 35 g (0.12 mol, 48.3%, 96.9% of theory) of (S)-α-[(tert-butylsulfonyl)methyl]hydrocinnamic acid in the form of white crystals, which had an enantiomeric excess of >98%. In order to determine the purity by gas chromatography, the compound obtained was silylated and had a purity of >99%.

We claim:

1. A process for the preparation of optically pure (S)-α-[(tert-butylsulfonyl)methyl]hydrocinnamic acid of the formula which process comprises emulsifying a racemic (RS)-α[(tert-butylsulfonyl)methyl]hydrocinnamic acid ester of the formula

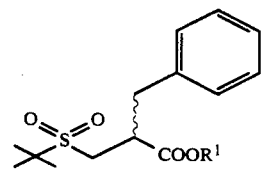

II wherein $R^1$ is $C_{1-4}$-alkyl, in an aqueous medium and reacting with a protease selected from the group consisting of α-chymotrypsin; Optimase- an alkaline protease obtained by the controlled fermentation of Bacillus licheniformis; Savinase- an endoprotease of the serine type produced by submerged fermentation of a microorganism which is an alkalophilic Bacillus species; and Alcalase- an endoprotease of the serine type produced by submerged fermentation of a microorganism which is a selected strain of Bacillus licheniformis, for the selective conversion of the racemic (RS)ester into the (S)-carboxylic acid, whereby the reaction is carried at a pH value between about 6.5 and about 8.5, and thereafter isolating the (R)-ester and the (S)-acid separately from the reaction medium.

2. The process in accordance with claim 1, wherein the ester of the formula

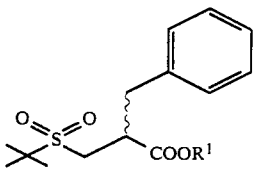

II is emulsified by melting at an elevated temperature.

3. The process in accordance with claim 2, wherein the emulsification is effected at a temperature of 35°–45° C.

4. The process in accordance with claim 1, wherein the reaction is carried out at a pH value of about 7.5.

5. The process in accordance with claim 1, wherein $R^1$ is ethyl.

6. The process in accordance with claim 1, wherein the aqueous medium contains calcium chloride.

7. The process in accordance with claim 1, wherein the protease is Optimase- an alkaline protease obtained by the controlled fermentation of Bacillus licheniformis; Savinase- an endoprotease of the serine type produced by submerged fermentation of a microorganism which is an alkalophilic Bacillus species; and Alcalase- an endoprotease of the serine type produced by submerged fermentation of a microorganism which is a selected strain of Bacillus licheniformis.

* * * * *